US010420465B1

(12) United States Patent
Stone et al.

(10) Patent No.: US 10,420,465 B1
(45) Date of Patent: Sep. 24, 2019

(54) OCULOMETRIC ASSESSMENT OF SENSORIMOTOR IMPAIRMENT

(71) Applicant: UNITED STATES OF AMERICA AS REPRESENTED BY THE ADMINISTRATOR OF NASA, Washington, DC (US)

(72) Inventors: Leland S. Stone, San Francisco, CA (US); Dorion B. Liston, Boulder Creek, CA (US)

(73) Assignee: United States of America as Represented by the Administrator of NASA, Washington, DC (US)

(*) Notice: Subject to any disclaimer, the term of this patent is extended or adjusted under 35 U.S.C. 154(b) by 0 days.

(21) Appl. No.: 15/707,561

(22) Filed: Sep. 18, 2017

Related U.S. Application Data

(60) Continuation-in-part of application No. 15/676,875, filed on Aug. 14, 2017, which is a division of application No. 14/710,260, filed on May 12, 2015, now Pat. No. 9,730,582.

(60) Provisional application No. 61/994,673, filed on May 16, 2014, provisional application No. 62/395,927, filed on Sep. 16, 2016.

(51) Int. Cl.
*A61B 3/00* (2006.01)
*A61B 3/032* (2006.01)
*A61B 3/113* (2006.01)

(52) U.S. Cl.
CPC ............ *A61B 3/113* (2013.01); *A61B 3/0025* (2013.01); *A61B 3/0041* (2013.01); *A61B 3/0091* (2013.01); *A61B 3/032* (2013.01)

(58) Field of Classification Search
CPC ...... A61B 3/113; A61B 3/0041; A61B 3/0091; A61B 3/032; A61B 3/0025; A61B 3/02
USPC .................. 351/209, 210; 382/103; 600/558; 345/156, 157
See application file for complete search history.

(56) References Cited

U.S. PATENT DOCUMENTS

| | | | | |
|---|---|---|---|---|
| 4,889,422 A | * | 12/1989 | Pavlidis | A61B 3/113 351/210 |
| 6,419,638 B1 | * | 7/2002 | Hay | A61B 3/0025 600/558 |
| 2010/0016754 A1 | * | 1/2010 | Whillock | A61B 3/113 600/558 |
| 2014/0171756 A1 | * | 6/2014 | Waldorf | A61B 3/032 600/301 |

(Continued)

OTHER PUBLICATIONS

"Oculometric Assesssment of Dynamic Visual Processing", Journal of Vision, 2014.*

*Primary Examiner* — Jordan M Schwartz
(74) *Attorney, Agent, or Firm* — Rhys W. Cheung; Robert M. Padilla

(57) ABSTRACT

Various conditions, such as traumatic brain injuries (TBI), diseases, injuries, and/or other impairments, may be diagnosed by deriving a sensitive overall indicator of impairment of sensorimotor functional status based on results of an eye-movement assessment test that includes an appropriately randomized, radial tracking task together with a broad set of oculometric measures. The oculometric measures may be combined to yield the sensitive overall indicator of a particular impairment state. More specifically, the oculometric measures may be vectorized to help diagnose both the type of TBI, disease, or impairment and the extent thereof.

18 Claims, 8 Drawing Sheets

(56) References Cited

U.S. PATENT DOCUMENTS

2017/0135577 A1\* 5/2017 Komogortsev ........ A61B 3/113

\* cited by examiner

FIG. 1B
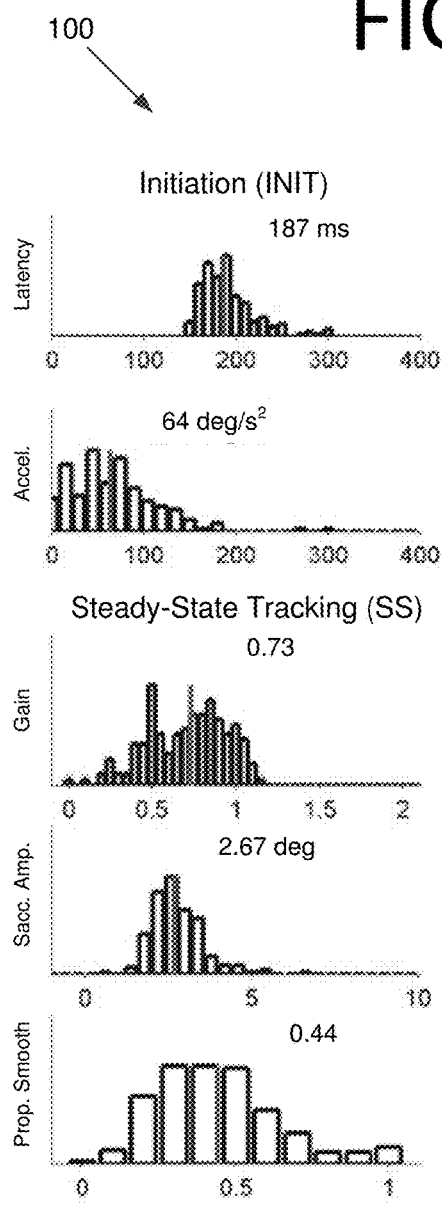
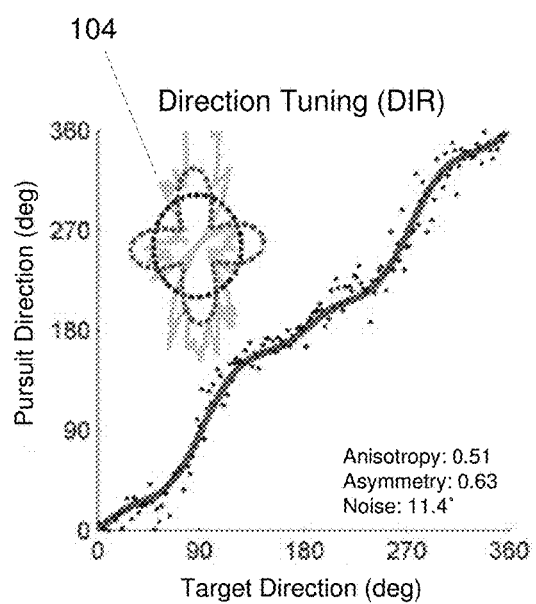
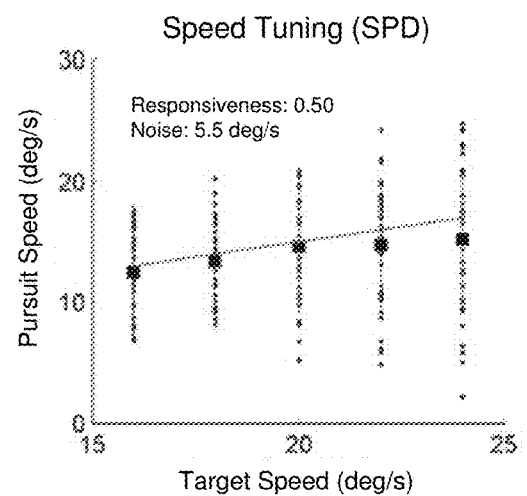

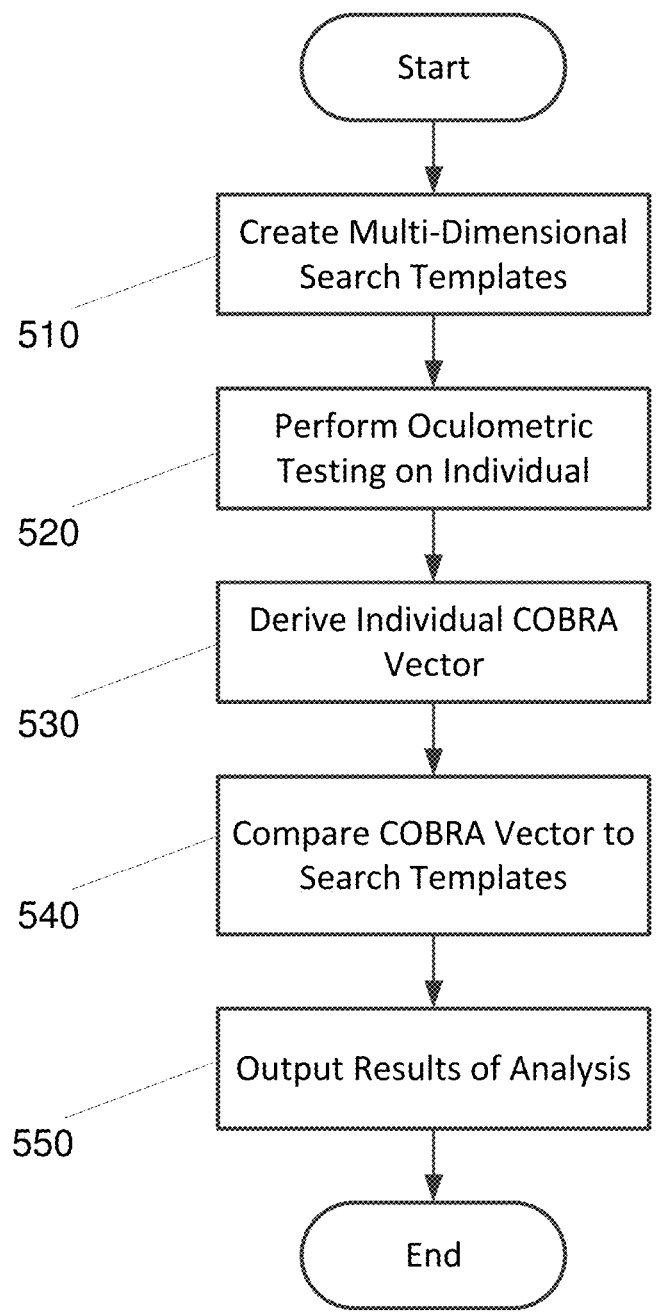

OCULOMETRIC ASSESSMENT OF SENSORIMOTOR IMPAIRMENT

CROSS-REFERENCE TO RELATED APPLICATION

This application is a continuation-in-part of U.S. patent application Ser. No. 15/676,875 filed Aug. 14, 2017, which is a divisional of U.S. patent application Ser. No. 14/710,260 filed May 12, 2015, now issued as U.S. Pat. No. 9,730,582, which claims the benefit of U.S. Provisional Patent Application No. 61/994,673 filed May 16, 2014. This application also claims the benefit of U.S. Provisional Patent Application No. 62/395,927 filed Sep. 16, 2016. The subject matter of these earlier filed applications is hereby incorporated by reference in its entirety.

ORIGIN OF THE INVENTION

The invention described herein was made in the performance of work under a NASA contract by an employee of the San Jose State University Research Foundation and by an employee of the United States Government and is subject to the provisions of Public Law 96-517 (35 U.S.C. § 202) and may be manufactured and used by or for the Government for governmental purposes without the payment of any royalties thereon or therefore. In accordance with 35 U.S.C. § 202, the contractor elected not to retain title.

FIELD

The present invention generally relates to neuro-functional assessment, and more particularly, to oculometric assessment of sensorimotor impairment.

BACKGROUND

Diffuse tissue damage from impact or blast traumatic brain injury (TBI), various illnesses, intoxication due to drugs or alcohol, sleep deprivation, and the like degrade information processing by the brain, often resulting in impairments in sensorimotor function. Deficits in dynamic visual processing and smooth-pursuit tracking can indicate that such an impairment exists. Indeed, eye movements are the most frequent, biomechanically-simplest, voluntary, visually-driven motor responses, providing a model system to assess the sequelae of brain insult, injury, and impairment. For more than a century, neurologists, psychologists, and psychiatrists have recognized that oculomotor behavior can reflect functional consequences of neural pathology, resulting in an extensive catalogue of qualitative oculomotor signs of drug toxicity, brain injury, and neurological disease, as well as standard ranges for normal behavior on common tasks.

Thus, oculomotor exams are used in both clinical (e.g., localizing lesions, diagnosing vestibular disorders, and detecting cranial nerve palsies) and field (e.g., detecting alcohol intoxication and fatigue) settings. Following TBI, oculomotor signs, such as disconjugate gaze, impaired saccadic inhibition, increased movement latency, amplified directional error, and impaired predictive tracking, have been reported, all consistent with impaired visual processing. However, the need for a readily-available clinical tool to quantitatively and systematically assess motion processing persists. To this end, leaders in the oculomotor field have proposed using oculomotor metrics as biomarkers of disease or trauma.

Current oculometric approaches do not convert qualitative patterns of multi-dimensional deficits (e.g., prolonged latencies, sluggish accelerations, reduced gain, elevated direction noise, etc.) expressed in the raw native units of the measurements (e.g., ms, deg/s$^2$, etc.) into standardized normal units that can be used to make meaningful comparisons of the severity of deficits across these disparate dimensions (and associated disparate units), as well as to combine these multiple individual deficits into a single scalar measure of overall impairment specific to a particular potential disease or injury state. Accordingly, an improved approach to the processing of multi-variate oculomotor data used to detect and characterize sensorimotor impairment may be beneficial.

SUMMARY

Certain embodiments of the present invention may provide solutions to the problems and needs in the art that have not yet been fully identified, appreciated, or solved by conventional clinical neuro-functional processing assessment technologies. For example, some embodiments of the present invention pertain to diagnosing a condition by deriving a sensitive indicator of the likelihood of a particular disease or injury state based on results of an eye-movement assessment test that includes an appropriately randomized, radial tracking task together with a broad set of oculometric measures. The set of oculometric measures may be combined into a single scalar to yield the sensitive overall indicator of sensorimotor functional status. More specifically, for any given clinical condition, an "impairment vector" may be defined by the direction of the deviation in the multi-dimensional space of oculomotor measures between the mean of the relevant specific patient population and the mean of the normal population. The inner product between such a specific impairment vector and the multi-dimensional oculomotor performance vector of any individual yields a linear detection metric of the severity of their impairment (i.e., their "impairment index") along the tested impairment vector with specificity potentially further enhanced through the absence or paucity of impairment along other tested "impairment vector" directions.

In some embodiments, the impairment vector for TBI could be used to measure an individual's likelihood of having suffered from a TBI by showing that the TBI index (a specific impairment index, see below) is significantly elevated compared to that of the normal population (or with respect to a baseline measure from the same individual). Further specificity in such a suggested diagnosis could be achieved by measuring other impairment indices associated with other impairment vectors. For example, an alcohol intoxication index or a fatigue index could be computed using the alcohol and fatigue vectors, respectively, to determine the relative likelihood that observed symptoms or deficits might be caused by factors other than TBI, such as alcohol or fatigue.

In an embodiment, a computer-implemented method includes creating search templates for a plurality of conditions, by a computing system, and performing oculometric testing on an individual, by the computing system. The computer-implemented method also includes creating a vector for the individual, by the computing system, based on the oculometric testing, and analyzing the vector for the individual, by the computing system, against one or more of the search templates to produce an impairment index that maps the vector for the individual to the one or more search templates. The computer-implemented method further includes outputting results of the analysis for review, by the computing system.

In another embodiment, a computer program is embodied on a non-transitory computer-readable medium. The program is configured to cause at least one processor to perform oculometric testing on an individual and create a vector for the individual based on the oculometric testing. The computer program is also configured to cause the at least one processor to analyze the vector for the individual against a search template to produce an impairment index that maps the vector for the individual to the search template and output results of the analysis for review.

In yet another embodiment, a computing system includes memory storing computer program code for performing oculometric assessment of sensorimotor impairment and at least one processor configured to execute the computer program code. The computing system is configured to perform oculometric testing on an individual and create a vector for the individual based on the oculometric testing. The computing system is also configured to analyze the vector for the individual against a search template and produce an impairment index based on the analysis that maps the vector for the individual to the search template.

In a further embodiment, a computer-implemented method includes displaying a tracking target, by a computing system, at an initial location on a display for a randomized delay interval. After the randomized delay interval has elapsed, the method includes moving the tracking target in a step, by the computing system, to a random location on the display; moving the tracking target on the display, by the computing system, from the random location on the display towards the initial location at least until the tracking target crosses the initial location; periodically measuring, by the computing system, user eye position while the user is following the tracking target, and repeating the moving of the tracking target and eye position measurement, by the computing system, a plurality of times. The method also includes analyzing the user eye response measurements, by the computing system, to determine a plurality of quantitative performance measures; and outputting, by the computing system, results of the analysis, wherein the plurality of quantitative performance measurements comprise a cloverleaf as a measure of the user's own idiosyncratic oblique effect that provides a pattern uniquely identifying the user.

The cloverleaf as a measure of the user's own idiosyncratic oblique effect provides a baseline for the same user to determine deviation from normal performance for the user; provides a measurement of user performance against a reference population of performance metrics from normal human subjects to determine a deviation from normal for the user; provides a measurement of peripheral vision, prediction, asymmetry between eye performance, or any combination thereof, to determine a type and a degree of brain injury, a progression of disease, whether the user is faking an injury, whether the user is consciously failing to perform the task, or whether the user is intoxicated; and provides a baseline measurement from the same user for an injury to determine whether the user is faking the injury.

The computer-implemented method further includes comparing, by the computing system, a previous cloverleaf for the user to a current cloverleaf to determine whether the user is improving, deteriorating, or remaining the same.

In another embodiment, a computer-implemented method includes displaying a tracking target, by a computing system, at an initial location on a display for a randomized delay interval. After the randomized delay interval has elapsed, the method includes moving the tracking target in a step, by the computing system, to a random location on the display; moving the tracking target on the display, by the computing system, from the random location on the display towards the initial location at least until the tracking target crosses the initial location; periodically measuring, by the computing system, user eye position while the user is following the tracking target; and repeating the moving of the tracking target and eye position measurement, by the computing system, a plurality of times. The method also includes analyzing the user eye response measurements, by the computing system, to determine a plurality of quantitative performance measures; and outputting, by the computing system, results of the analysis, wherein the plurality of quantitative performance metrics comprise at least one metric for quantifying vigor of pursuit initiation and at least one metric for quantifying a quality of steady-state tracking.

The at least one metric for quantifying the vigor of the pursuit initiation quantifies latency and acceleration and quantifies gain, saccade amplitude, and proportion smooth. The metrics for quantifying vigor of pursuit initiation and quantifying the quality of steady-state tracking provide a baseline for the same user to determine deviation from normal performance for the user; provide a measurement of user performance against a reference population of performance metrics from normal human subjects to determine a deviation from normal for the user; provide a measurement of peripheral vision, prediction, asymmetry between eye performance, or any combination thereof, to determine a type and a degree of brain injury, a progression of disease, whether the user is faking an injury, whether the user is consciously failing to perform the task, or whether the user is intoxicated; and provide a baseline measurement from the same user for an injury to determine whether the user is faking the injury.

The computer-implemented method further includes comparing, by the computing system, the metrics for quantifying vigor of pursuit initiation and quantifying the quality of steady-state tracking against previous measurements for the user to determine whether the user is improving, deteriorating, or remaining the same.

In yet a further embodiment, a computer-implemented method includes displaying a tracking target, by a computing system, at an initial location on a display for a randomized delay interval. After the randomized delay interval has elapsed, the method includes moving the tracking target in a step, by the computing system, to a random location on the display; moving the tracking target on the display, by the computing system, from the random location on the display towards the initial location at least until the tracking target crosses the initial location; periodically measuring, by the computing system, user eye position while the user is following the tracking target; and repeating the moving of the tracking target and eye position measurement, by the computing system, a plurality of times. The method also includes analyzing the user eye response measurements, by the computing system, to determine a plurality of quantitative performance measures; and outputting, by the computing system, results of the analysis, wherein the plurality of quantitative performance metrics comprise a direction of pursuit response, and a fitting function to describe a shape of a cloverleaf is determined by $$f(\varphi)=1+\alpha\cdot\cos(4\varphi+\Delta))-\beta\cdot\cos(2\varphi+\Delta))$$

where α describes a magnitude of cardinal-oblique anisotropy, β describes asymmetry between a size of vertical and horizontal lobes, and Δ describes an orientation of the cloverleaf.

The direction of pursuit response provides a baseline for the same user to determine deviation from normal performance for the user; provides a measurement of user performance against a reference population of performance metrics from normal human subjects to determine a deviation from normal for the user; provides a measurement of peripheral vision, prediction, asymmetry between eye performance, or any combination thereof, to determine a type and a degree of brain injury, a progression of disease, whether the user is faking an injury, whether the user is consciously failing to perform the task, or whether the user is intoxicated; and provides a baseline measurement from the same user for an injury to determine whether the user is faking the injury.

The computer-implemented method further includes comparing, by the computing system, the direction of pursuit response against previous measurements for the user to determine whether the user is improving, deteriorating, or remaining the same.

In a further embodiment, a system includes a computing system having a display, the computing system configured to display a tracking target on the display, and an eye tracker configured to take periodic measurements of eye position of a user based on the displayed tracking target position, wherein the computing system is further configured to: receive the periodic measurements from the eye tracker, and analyze the received periodic measurements to determine a plurality of quantitative performance measurements and display the eye position measurements and/or results of the analysis, or transmit the received periodic measurements to another computing system that analyzes the received periodic measurements to determine the plurality of quantitative performance measurements, wherein the plurality of quantitative performance measurements includes at least one metric for quantifying vigor of pursuit initiation and at least one metric for quantifying a quality of steady-state tracking.

The plurality of quantitative measurements includes direction tuning, speed tuning, or any combination or subset thereof. The at least one metric for quantifying the vigor of the pursuit initiation quantifies latency and acceleration and quantifies gain, saccade amplitude, and proportion smooth. The metrics for quantifying vigor of pursuit initiation and quantifying the quality of steady-state tracking provide a baseline for the same user to determine deviation from normal performance for the user; provide a measurement of user performance against a reference population of performance metrics from normal human subjects to determine a deviation from normal for the user; provide a measurement of peripheral vision, prediction, asymmetry between eye performance, or any combination thereof, to determine a type and a degree of brain injury, a progression of disease, whether the user is faking an injury, whether the user is consciously failing to perform the task, or whether the user is intoxicated; and provide a baseline measurement from the same user for an injury to determine whether the user is faking the injury.

The system further includes comparing, by the computing system, the metrics for quantifying vigor of pursuit initiation and quantifying the quality of steady-state tracking against previous measurements for the user to determine whether the user is improving, deteriorating, or remaining the same.

In another embodiment, a system includes a computing system having a display, the computing system configured to display a tracking target on the display and an eye tracker configured to take periodic measurements of eye position of a user based on the displayed tracking target position, wherein the computing system is further configured to: receive the periodic measurements from the eye tracker, and analyze the received periodic measurements to determine a plurality of quantitative performance measurements and display the eye position measurements and/or results of the analysis, or transmit the received periodic measurements to another computing system that analyzes the received periodic measurements to determine the plurality of quantitative performance measurements, wherein the plurality of quantitative performance measurements includes a cloverleaf as a measure of the user's own idiosyncratic oblique effect that provides a pattern uniquely identifying the user.

The cloverleaf as a measure of the user's own idiosyncratic oblique effect provides a baseline for the same user to determine deviation from normal performance for the user; provides a measurement of user performance against a reference population of performance metrics from normal human subjects to determine a deviation from normal for the user; provides a measurement of peripheral vision, prediction, asymmetry between eye performance, or any combination thereof, to determine a type and a degree of brain injury, a progression of disease, whether the user is faking an injury, whether the user is consciously failing to perform the task, or whether the user is intoxicated; and provides a baseline measurement from the same user for an injury to determine whether the user is faking the injury.

The system further includes comparing, by the computing system, a previous cloverleaf for the user to a current cloverleaf to determine whether the user is improving, deteriorating, or remaining the same.

In yet another embodiment, a computer program embodied on a non-transitory computer-readable medium causes at least one processor to receive a plurality of eye position measurements tracking a user's following of a tracking target over time. The program also analyzes the plurality of eye position measurements to determine a plurality of quantitative metrics, or transmit the plurality of eye position measurements to a remote computing system to analyze the plurality of eye position measurements and determine the plurality of quantitative metrics. Based on the plurality of quantitative metrics, the program provides an indication of whether the user has a brain injury, whether the user has a disease, whether the user is faking an injury, whether the user is intoxicated, or any combination thereof, wherein the plurality of quantitative performance metrics comprise a direction of pursuit response, and a fitting function to describe a shape of a cloverleaf is determined by $$f(\varphi)=1+\alpha \cdot \cos(4\varphi+\Delta))-\beta \cdot \cos(2\varphi+\Delta))$$

where α describes a magnitude of cardinal-oblique anisotropy, β describes asymmetry between a size of vertical and horizontal lobes, and Δ describes an orientation of the cloverleaf.

The direction of pursuit response provides a baseline for the same user to determine deviation from normal performance for the user; provides a measurement of user performance against a reference population of performance metrics from normal human subjects to determine a deviation from normal for the user; provides a measurement of peripheral vision, prediction, asymmetry between eye performance, or any combination thereof, to determine a type and a degree of brain injury, a progression of disease, whether the user is faking an injury, whether the user is consciously failing to perform the task, or whether the user is intoxicated; and provides a baseline measurement from the same user for an injury to determine whether the user is faking the injury.

The computer program further includes comparing, by the computing system, the direction of pursuit response against previous measurements for the user to determine whether the user is improving, deteriorating, or remaining the same.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 1B illustrates graphs of COBRA oculometric measurements for a TBI subject, according to an embodiment of the present invention.

FIG. 5 is a flowchart illustrating a process for determining a type and severity of an individual's condition, according to an embodiment of the present invention.

DETAILED DESCRIPTION OF THE EMBODIMENTS

Figure 1A:
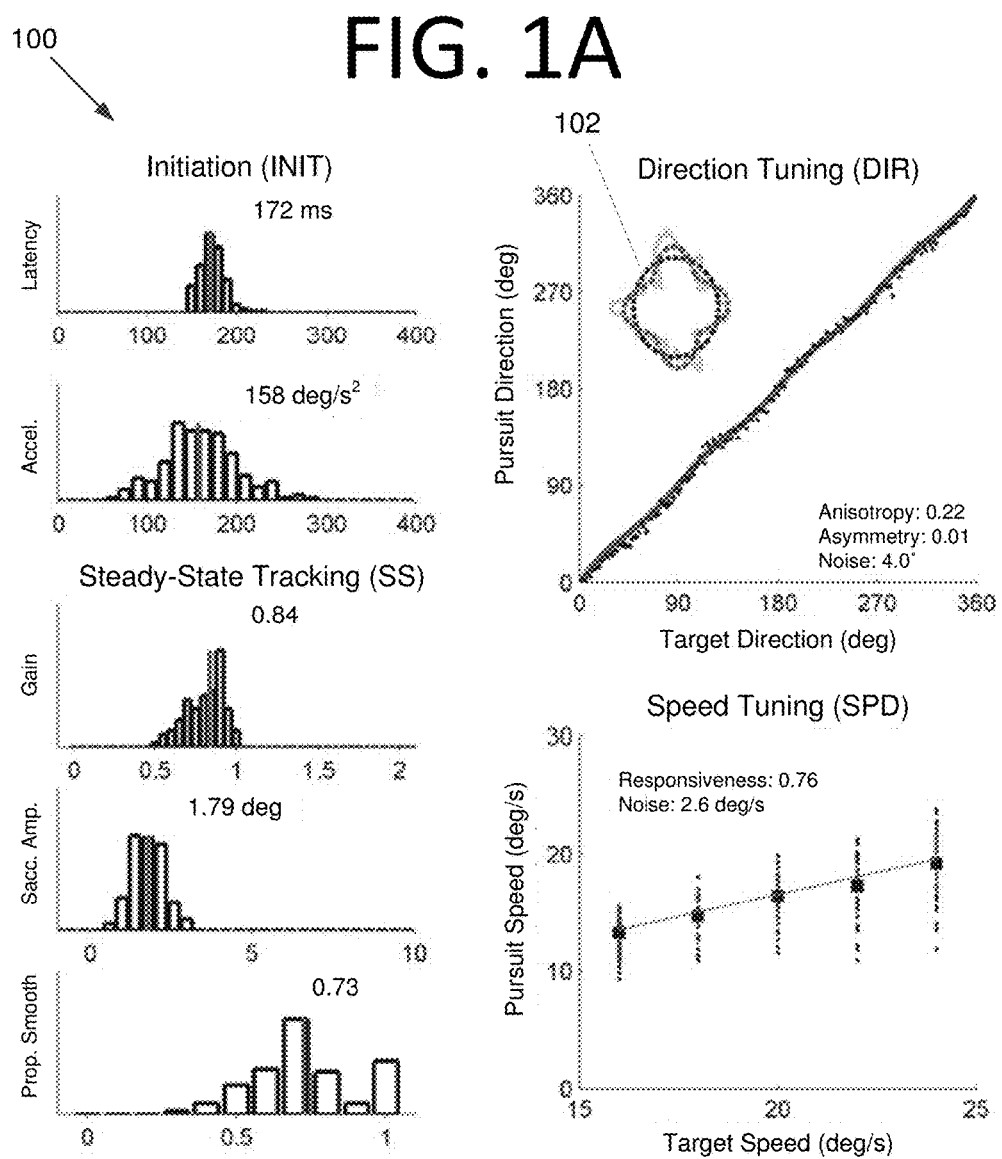
FIG. 1A illustrates graphs of Comprehensive Oculometric Behavioral Response Assessment (COBRA) oculometric measurements for a typical control subject, according to an embodiment of the present invention.

Some embodiments of the present invention pertain to diagnosing a condition by deriving a sensitive indicator of the likelihood of a particular disease or injury state based on results of an eye-movement assessment test that includes an appropriately randomized, radial tracking task together with a broad set of oculometric measures. The oculometric measures may be combined to yield the sensitive overall indicator of sensorimotor functional status. More specifically, the oculometric measures may be vectorized to help diagnose both the type of disease, injury, or impairment and the extent thereof.

Based on experimentation, search templates for TBI, diseases, and other sources of impairments may be derived using data, such as Comprehensive Oculometric Behavioral Response Assessment (COBRA) expressed in a 10-dimensional space of metrics (or any n-dimensional space without deviating from the scope of the invention). More specifically, individuals with a certain condition may be tested and an "average" representation across such a population may be developed for their condition. The severity of the TBI, disease, or impairment for an individual can then be quantified as single scalar value. This solves the problem of converting a complex qualitative pattern of deficits (e.g., prolonged latencies, sluggish accelerations, reduced gain, elevated direction noise, etc.) expressed in the native units of the measurements (e.g., milliseconds (ms), deg/s^2, etc.) into a single metric based on the combination of standard normalized units. Used in combination with a reference database from a population of normal (non-impaired) subjects, the "impairment vector" (a form of search template) quantitatively characterizes a complex pattern of symptoms across a population of similarly affected subjects (e.g., suffering from the same disease or injury) and the "impairment indices" computed from individuals using these "impairment vectors" quantify the severity of a disorder, or lack thereof, consistent with the candidate impairment.

For COBRA (or any oculometric technology like COBRA) to screen for neurological signs of disease and injury, a characteristic set of signs should be derived for each potential disease or injury of interest. Some embodiments give a recipe to compute this characteristic set of signs as well as the specific vector for traumatic brain injury (i.e., the "TBI vector"). The impairment vector or search template characterizes the disorder quantitatively, and the impairment indices derived from an individual's data quantify how severe the individual's disorder is.

A benefit of some embodiments is that an n-dimensional space of metrics may be reduced to a vector, which has both a direction and an amplitude. COBRA is currently a 10-dimensional space, but any other number of metrics may be used without deviating from the scope of the invention. By comparing the vector of a tested individual to search templates (i.e., average or characteristic vectors) for different TBI types, diseases, and/or impairments (e.g., alcohol or drug intoxication, sleep deprivation, etc.), it can be discerned with a reasonable probability which condition or conditions an individual is likely to have, as well as how severe the individual's condition is. Generally, the data from individuals with a given condition will point in the same basic direction and amplitude. This enables condition and severity identification for a previously untested individual whose condition may be unknown.

The vectors or search templates for different TBI, diseases, and impairments can be used to determine the likelihood of that impairment. In some cases, conditions that are not necessarily intuitive as being detectable via visual testing (e.g., diabetes) may be diagnosed. The larger the projection of an individual's oculomotor performance vector onto a given condition's impairment vector, the higher the likelihood that the individual ha the condition associated with that impairment vector.

Some embodiments have advantages over conventional TBI, disease, and impairment detection technologies. Indeed, some embodiments change diagnostic technology from merely detecting whether an impairment exists to determining whether the impairment fits the complex multidimensional pattern associated with a specific condition. How the individual deviates from a general population with a condition may also be measured. This provides a discriminatory capability that can characterize the deficit (i.e., aid in actual diagnosis) as opposed to merely detecting it (i.e., determine that the person is suffering from something).

Per the above, the direction and amplitude of the individual's vector may define the "flavor" of the condition. For instance, the individual's data may project onto a specific impairment vector (e.g., the glaucoma vector) to yield an impairment index of X, suggesting an elevated likelihood of glaucoma. With enough dimensions, a range of individual conditions may be readily distinguishable from one another by yielding lower values of the indices associated with projections onto the impairment vector related to other conditions (e.g., TBI, sleep deprivation, retinitis pigmentosa, etc.). Additionally or alternatively, some embodiments may help to focus testing and speed diagnosis. For instance, if an individual maps X to glaucoma, but further testing by an ophthalmologist reveals that this is not the actual condition, the ophthalmologist can move to additional tests for the next most likely condition (i.e., with the next highest impairment index below X), and the next, and so on, until the actual condition is properly diagnosed.

Another advantage of some embodiments is that non-obvious conditions may be detected and identified very early in their progression, increasing the chance that the progression can be reversed, stopped, or slowed. By the time imaging reveals a condition, it is usually quite severe. Furthermore, in certain environments where multiple causes for a deficit are possible, the true cause can be determined. For instance, where a soldier has been subjected to a blast and has also been up for 48 straight hours, it can be determined which of these causes (or both) is the actual culprit for his or her deficits. Sleep deprivation looks significantly different from TBI due to blast trauma. Trucking companies could also employ such a test to clear their drivers for operation. While trucking companies themselves may be hesitant to spend the potential additional time and cost, insurance companies may drive them to do so. Also, law enforcement could use certain embodiments for testing in the field to determine how intoxicated/impaired a given individual is due to marijuana or alcohol, for instance, or whether their impairment results from another condition (e.g., sleep deprivation).

Per the above, some embodiments employ COBRA that derives various quantitative oculometrics from the test, which are then used for the assessment. Following calibration, subjects participate in an eye-movement tracking task including a certain number of trials (e.g., 180 trials). A chin and forehead rest may be used for head stabilization. On each trial in some embodiments, a radial version of Rashbass step-ramp motion is then displayed, whereby the target makes a step in a random direction from a central fixation location, then moved back through the original location at a constant velocity (e.g., 16-24 deg/s). The speed, direction, onset-timing, and duration of target motion may be independently randomized to promote uniform distribution of attention across space, time, and direction and to defeat strategies using anticipatory or predictive eye movements.

TBI and Experimental Control Populations

In an experiment that was conducted, 34 TBI subjects were recruited from local medical facilities and brain injury rehabilitation centers who met the following requirements: (i) security rules allowed them access to NASA Ames Research Center (US citizen); (ii) aged between 18-70 years old; (iii) self-reported nonpenetrating impact trauma to the head, verified using the Ohio State University TBI Identification Method; (iv) able to make their own medical decisions and sign informed consent forms; (v) able to sit still for 20 minutes, fixate for several seconds at a time and track with the left eye while keeping their head still; (vi) able to sit, stand, and walk without assistance; and (vii) better than 20/200 visual acuity. Subjects completed a survey to document their age, gender, whether they needed glasses or contacts, when they were diagnosed, when they were injured, and a self-reported assessment of the severity of their current condition, with 1 being "little to no residual injury" and 10 being "completely disabled". The causes of injuries sustained by this TBI population varied in both type and severity, including: unspecified injuries (5 subjects), motor vehicle accidents (18 subjects), falls (1 subject), bicycle or skateboarding accidents (8 subjects), and assault (2 subjects). Of the 25 TBI subjects who reported their TBI on the mild-moderate-severe scale, 2 reported mild TBI, 5 reported moderate TBI, 3 reported moderate-to-severe TBI, and 15 reported severe TBI.

The subject population reported loss of consciousness (LOC) ranging in duration from no LOC to two months in a coma. Using the durations provided by the Ohio State University TBI Identification Method, 2 subjects reported no LOC, 7 subjects reported LOC less than 30 minutes, 1 subject reported LOC between 30 minutes and 24 hours, and 24 subjects reported LOC greater than 24 hours. The Freiburg Visual Acuity Test was used to measure binocular visual acuity. For the 34-subject TBI population (21 males, 13 females) ranging in age from 20 to 61 years ($10^{th}$ percentile: 23 years, $25^{th}$ percentile: 26 years, $50^{th}$ percentile: 34 years, $75^{th}$ percentile: 49 years, $90^{th}$ percentile: 57 years), the mean time since injury was 9.1 years (range: 6.9 months to 32.2 years; $10^{th}$ percentile: 1.0 year, $25^{th}$ percentile: 3.6 years, $50^{th}$ percentile: 6.1 years, $75^{th}$ percentile: 16.1 years, $90^{th}$ percentile: 19.0 years) and the mean self-reported severity level was 3.3 (range: 1-7), with static visual acuity ranging from −0.28 to 0.44 (median: −0.08).

The 41-subject control population (22 males, 19 females) ranging in age from 20 to 56 years ($10^{th}$ percentile: 22 years, $25^{th}$ percentile: 24 years, $50^{th}$ percentile: 27 years, $75^{th}$ percentile: 35 years, $90^{th}$ percentile: 51 years) had static visual acuity ranging from −0.29 to 0.44 (median: −0.20). Although the age distribution of control subjects was skewed toward younger ages and the distribution of ages of TBI subjects was more uniform, the difference in age between the two populations was only borderline significant (p=0.052, Wilcoxon rank sum test). Although the control population was not screened for history of brain injury, any unknown injuries in the control population would only serve to underestimate the TBI detectability using COBRA.

TBI Vector and TBI Impairment Index

To characterize the TBI-related signs present in the task, a previously-described baseline data set was used as a normative standard. First, a set of ten measurements from each subject was considered in their native units (e.g., ms, deg, deg/s², etc.) as a raw COBRA vector. The raw measurements were then converted into z-values (units of standard deviation to allow for comparison across the disparate dimensions) relative to the control data set by subtracting the median and scaling by the estimated standard deviation:

$$\omega = \frac{RAW - CONTROL_{50th}}{\sigma} \quad (1)$$

where $$\sigma = \frac{(CONTROL_{75th} - CONTROL_{25th})}{2 \cdot \Phi^{-1}(0.75)}$$

and $\Phi^{-1}$ is the inverse of the normal cumulative distribution function. For the steady-state gain metric, an arcsin correction was applied to de-skew the raw data. Lastly, the sign for the latency, speed noise, saccadic amplitude, and direction noise metrics was flipped so that negative values indicate impairment. Normalized metrics (ω) with higher values correspond to faster, quicker, smoother, higher-gain, and more accurate tracking. Lower values correspond to slower, less accurate movements with larger and more frequent saccades. For these analyses, a 10-element COBRA vector of normalized metrics was used:

$$COBRA = \begin{bmatrix} \omega_{INIT\ latency} \\ \omega_{INIT\ accel} \\ \omega_{SS\ gain} \\ \omega_{SS\ sacc\ amp} \\ \omega_{SS\ prop\ smooth} \\ \omega_{DIR\ anisotropy} \\ \omega_{DIR\ assymetry} \\ \omega_{DIR\ noise} \\ \omega_{SPD\ responsiveness} \\ \omega_{SPD\ noise} \end{bmatrix} \quad (2)$$

In COBRA, INIT is initialization, DIR is direction tuning, SS is steady-state tracking, and SPD is speed tuning. However, direction-tuning anisotropy and asymmetry metrics were excluded when the level of direction noise exceeded 25° (4 of 34 TBI subjects) because the fits that yield these two metrics became numerically unstable and unreliable.

To characterize TBI-related oculomotor signs, COBRA vectors were averaged across the TBI population to yield a TBI vector:

$$TBI = \sum_{i=1}^{n} \frac{(COBRA_i)}{n} \quad (3)$$

Where n is the number of TBI subjects. Because the COBRA vectors are "normalized", each element of the TBI vector gives the distance (in standard deviation units or z-values) between the average TBI subject and the average of the control population, defined as the origin. For example, if there were no effect for a given metric, the mean of the TBI population would fall near zero along that axis. While more complicated formulations (e.g., a vector based on signal-to-noise) may afford incrementally-better statistical power, the most intuitive definition of the TBI vector was used for this example.

To quantify the scalar magnitude of the functional impairment along the TBI vector, the dot product was taken between an individual's COBRA vector and the TBI vector to yield a cross-correlation-based scalar metric:

$$TBI\ \text{Impairment Index} = \frac{COBRA \cdot TBI}{SCALING\ FACTOR} \quad (4)$$

$$SCALING\ FACTOR = \|CHOL(COV(CONTROL)) \cdot TBI'\|$$

The scaling factor in the denominator ensures a standard normal distribution of TBI impairment indices for the control population and scales the resulting index in standard deviation units of the control population. CHOL is the Cholesky Decomposition, COV(CONTROL) is the covariance matrix created by the entire set of COBRA vectors of the control population, and TBI' is the transpose of the TBI vector.

Results

The oculometric approach applied in this example yields a ten-dimensional summary of an individual's performance on the tracking task, for both control and TBI subjects. FIGS. 1A and 1B illustrate graphs 100 of COBRA oculometric measurements for a typical control subject and a TBI subject, respectively, according to an embodiment of the present invention. Histograms in the left-hand columns of both FIGS. 1A and 1B plot across-trial measurements of standard measures of pursuit performance. Direction-tuning and speed-tuning measurements of visual motion processing are shown in the right-hand columns. Pursuit initiation (INIT) measurements yield a skewed distribution of latencies and a quasi-normal distribution of accelerations. Steady-state (SS) tracking measurements (400 to 700 ms after motion onset) include: pursuit gain (ratio of eye speed to target speed), the average amplitude of saccades, and the proportion of total eye displacement that was smooth. The direction-tuning (DIR) plot shows pursuit direction as a function of target direction for each trial. The insets 102, 104 illustrate the "cloverleaf" direction-gain anisotropy and asymmetry 106 (gray line) referenced to the circle of unity gain (thin black line).

Qualitative comparison of FIGS. 1A and 1B captures some of the functional consequences of TBI-related tissue damage seen in the raw data. The control and TBI subjects shown highlight typical TBI-related oculomotor tracking deficits: longer latency, lower initial acceleration, lower steady-state gain, larger saccades, and a lower proportion of smooth movement. Obvious impairments in this TBI subject include high direction noise, large distortion in the direction-tuning function and low speed-tuning responsiveness. Although these two subjects are drawn from populations with substantial across-subject variance, the overall results demonstrate degraded tracking for the TBI population. See Table 1 below.

TABLE 1

DISTRIBUTIONS OF COBRA OCULOMETRICS FOR CONTROL AND TBI POPULATIONS

| | Control Population | | | | TBI Population | | | |
|---|---|---|---|---|---|---|---|---|
| | $25^{th}$ | $50^{th}$ | $75^{th}$ | σ | $25^{th}$ | $50^{th}$ | $75^{th}$ | σ |
| INIT Latency (ms) | 176 | 180 | 185 | 7 | 182 | 187 | 191 | 7 |
| INIT acceleration (deg/s$^2$) | 92 | 124 | 143 | 38 | 52 | 69 | 93 | 30 |
| SS Gain | 0.75 | 0.82 | 0.86 | 0.08 | 0.52 | 0.66 | 0.74 | 0.16 |
| SS Sacc. Amp. (deg) | 1.96 | 2.29 | 2.69 | 0.54 | 2.37 | 2.65 | 2.98 | 0.45 |
| SS Prop Smooth | 0.62 | 0.67 | 0.75 | 0.09 | 0.39 | 0.48 | 0.59 | 0.15 |
| DIR Anisotropy | 0.27 | 0.37 | 0.48 | 0.16 | 0.23 | 0.36 | 0.52 | 0.21 |

TABLE 1-continued

DISTRIBUTIONS OF COBRA OCULOMETRICS FOR CONTROL AND TBI POPULATIONS

| | Control Population | | | | TBI Population | | | |
|---|---|---|---|---|---|---|---|---|
| | $25^{th}$ | $50^{th}$ | $75^{th}$ | $\sigma$ | $25^{th}$ | $50^{th}$ | $75^{th}$ | $\sigma$ |
| DIR Asymmetry | 0.05 | 0.10 | 0.20 | 0.11 | −0.07 | 0.11 | 0.45 | 0.39 |
| DIR Noise (deg) | 6.62 | 8.66 | 11.10 | 3.32 | 7.65 | 11.78 | 15.75 | 6.01 |
| SPD Responsiveness | 0.42 | 0.55 | 0.65 | 0.17 | 0.10 | 0.22 | 0.41 | 0.23 |
| SPD Noise (deg/s) | 2.56 | 3.43 | 4.07 | 1.12 | 3.18 | 3.79 | 5.16 | 1.46 |
| Visual Acuity (LogMAR) | −0.23 | −0.20 | −0.11 | 0.09 | −0.15 | −0.08 | 0.13 | 0.21 |

"Log MAR" is the Logarithm of the Minimum Angle of Resolution. For each population, Table 1 gives the $25^{th}$, $50^{th}$, and $75^{th}$ percentile values for the ten oculometrics measured by the task, as well as the estimated standard deviation $\sigma$. For subjects with high levels of directional noise observed in the TBI population (25° or greater, 4 participants), the fitted anisotropy and asymmetry of the direction-tuning function (see FIGS. 1A and 1B) became unstable and have been omitted from the reported distributions (bold typeface cells).

Figure 2:
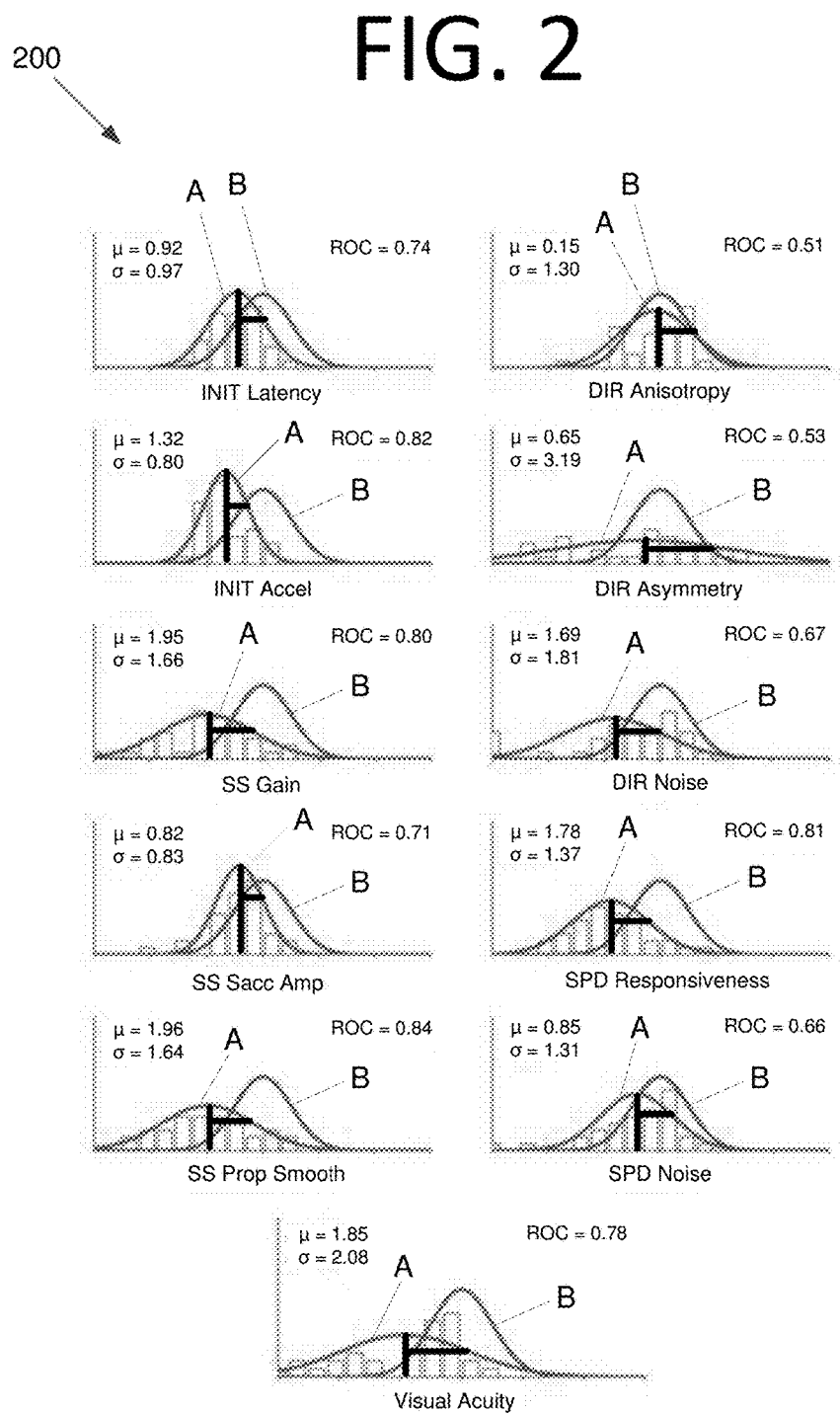
FIG. 2 illustrates graphs of the distributions of all ten COBRA metrics, as well as static visual acuity, according to an embodiment of the present invention.

To characterize the set of TBI-related deficits, the data was first normalized by the across-subject variance in the control population and then compared the distributions of values for TBI and control populations using an across-subject paradigm. Graphs 200 of FIG. 2 illustrate the distributions of all ten COBRA metrics and static visual acuity. Each graph plots the Gaussian fits to the distributions for control (B) and TBI (A) populations. The black unfilled histogram plots the values for the 34-subject TBI population. Inset into each set of axes are the mean and standard deviation for each of the TBI population's metrics, and the Receiver Operating Characteristic (ROC) curve area between the two distributions, which quantifies the ability of an ideal observer to discriminate one sample at random from one of the two distributions.

Figure 3:
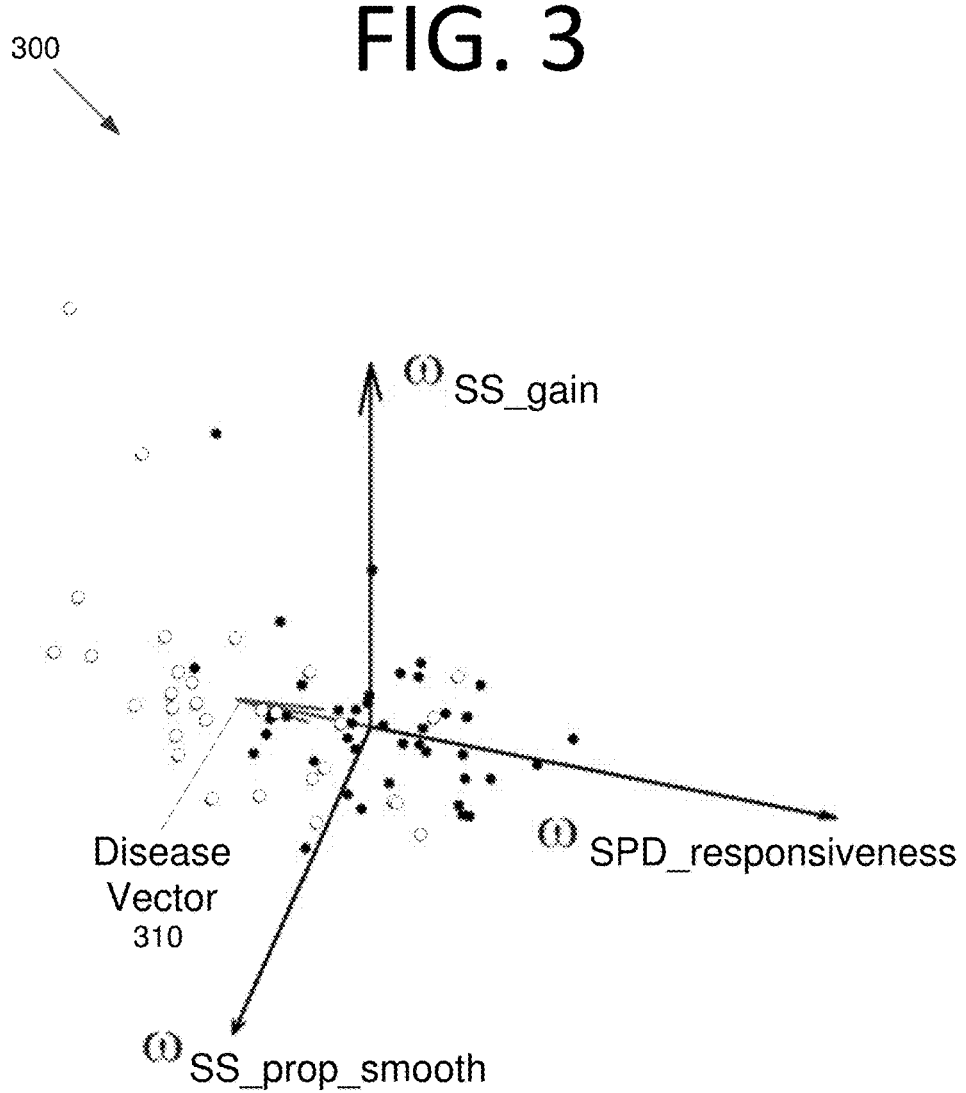
FIG. 3 is a scatterplot illustrating a three-dimensional subspace of a ten-dimensional dataset for control (filled circles) and TBI subjects (open circles), according to an embodiment of the present invention.

The TBI vector (see FIG. 3) is defined by the set of ten mean ($\mu$) values. More specifically, FIG. 3 illustrates a perspective two-dimensional (2D) rendering of a three-dimensional (3D) subspace showing the TBI vector in this subspace and the population of normal and injured subjects. It is not possible to graph the full TBI vector in a ten-dimensional (10D) space on 2D paper. However, the salient point is clear from the plot of the 3D subspace. TBI patients deviate systematically from normal along a particular direction in both this 3D subspace and in the 10D space that cannot be fully shown visually. Furthermore, this illustrates the problem of dealing with the full 10D (or more, in some embodiments) space of raw oculometric measures and motivates the need for extracting a single scalar measure from the full 10D (or more) space that still captures the critical information about how much any individual's 10D (or more) COBRA vector deviates from normal along the 10D (or more) direction defined by the TBI vector (i.e., a single measure that indicates that the person is likely to be within the TBI population). This was a motivation for inventing the "impairment index."

Considered separately, significant decrements were observed in the TBI population for six of the ten metrics (for initial acceleration, steady-state gain, steady-state proportion smooth, speed responsiveness, and steady-state saccade amplitude). A significantly lower static visual acuity was also observed for the TBI subjects (median: −0.08 Log MAR, 20/16 Snellen; range: −0.28 to 0.44, 20/11 to 20/55) with respect to the control population (median: −0.20 Log MAR, 20/13 Snellen; range: −0.29 to 0.44, 20/10 to 20/55), similar to previous reports. Overall, visual acuity was not significantly correlated with self-reported TBI severity ($p=0.127$, $r=-0.20$, Pearson's R) so acuity problems are not a significant factor in their self-reported impairment.

To evaluate the ability of the data to identify the TBI status of the subject without the benefit of individual baselines, two techniques from signal-detection theory were applied in an across-subject paradigm. First, the TBI vector (see TBI vector 310 in scatterplot 300 of FIG. 3) was defined to be the across-observer average of COBRA vectors for the TBI population, indicated by the gray vertical lines in FIG. 2. Scatterplot 300 shows a three-dimensional subspace of the ten-dimensional dataset for control subjects (black filled circles) and TBI subjects (black unfilled circles). A "TBI vector" (i.e., solid gray vector 310) was defined to point from the origin to the average across the TBI population. Two TBI data points fall right at the tip of TBI vector 310 and are difficult to segment from the arrowhead—one can be seen to occlude a nearby control data point, and the other can be seen as a gray fringe occluded by the same control data point. As TBI vector 310 gives the typical pattern of oculomotor signs observed with TBI subjects, the projection of any given subject's vector along the TBI vector, the subject's TBI impairment index, is an overall scalar measure of the severity of their impairment, scaled to the unit variance of the control population.

Figure 4A:
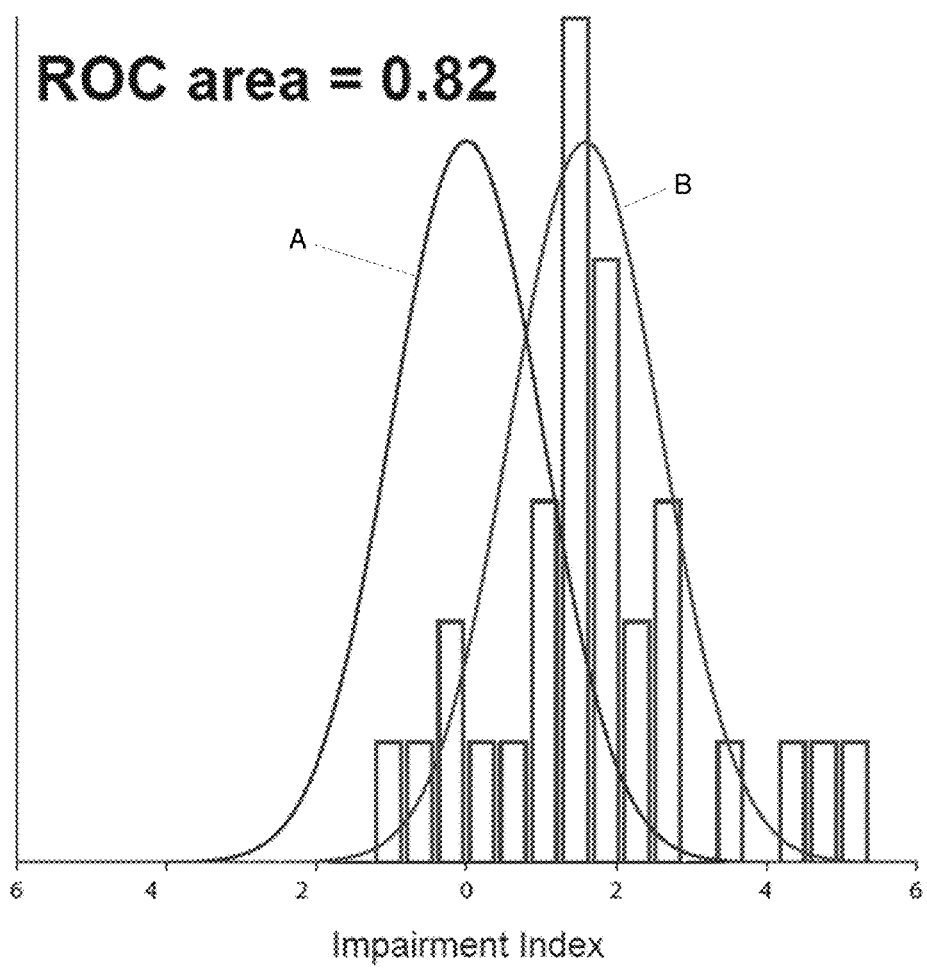
FIG. 4A is a histogram illustrating TBI impairment indices, according to an embodiment of the present invention.
Figure 4B:
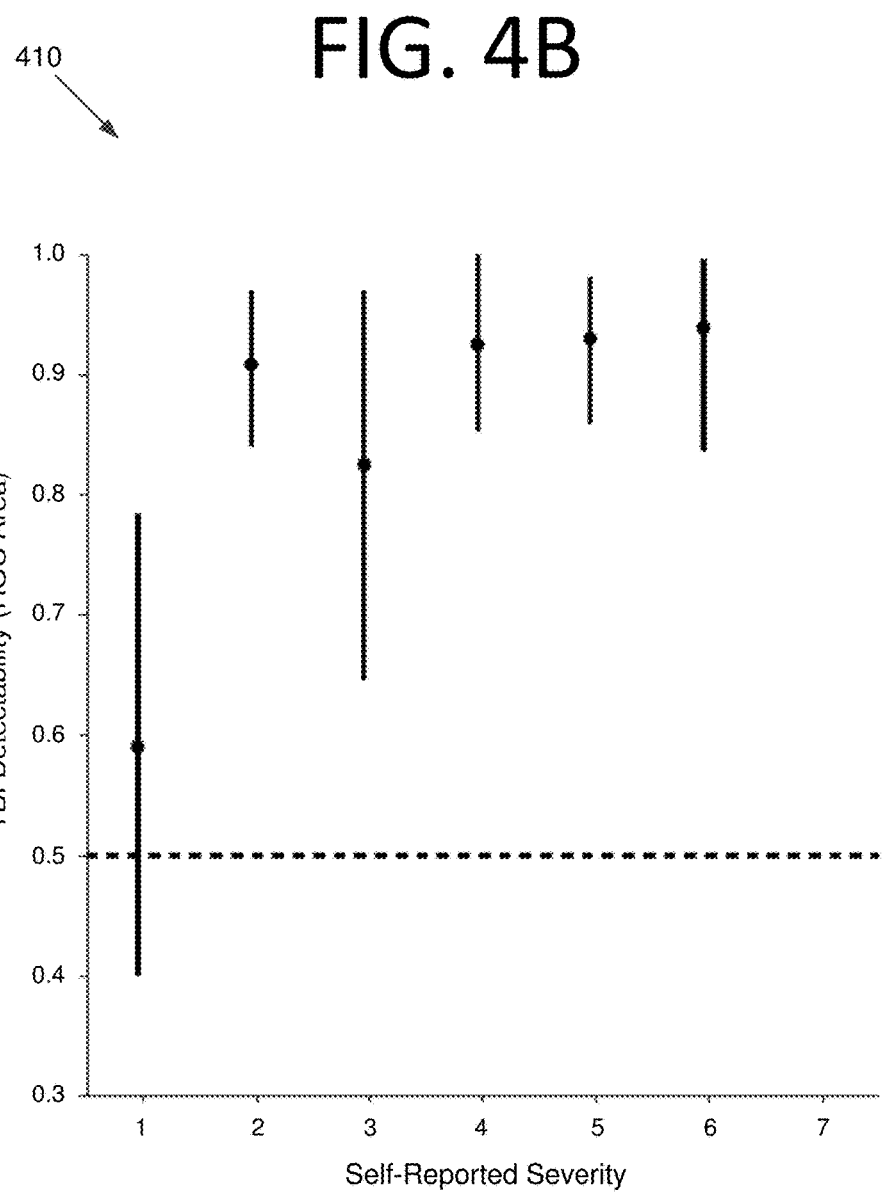
FIG. 4B is a graph illustrating the area under the Receiver Operating Characteristic (ROC) curves for each self-reported severity in the TBI population, according to an embodiment of the present invention.

Second, the TBI impairment index was computed (Eq. (4)) for each TBI and control subject. FIG. 4A is a histogram 400 illustrating the TBI impairment indices (gray unfilled bars) and fitted normal distribution (solid gray curve, B) for the population of 34 TBI subjects along with the normal distribution of the control population of 41 subjects (solid black curve, A). Graph 410 of FIG. 4B plots the measured ROC curve area for each the self-reported severity in the TBI population. Filled black circles plot the average of 1,000 bootstrapped measurements for each of the severity levels. Error bars show the central 90% of the bootstrapped distribution. Inset text shows the number of TBI subjects at each self-reported severity level.

This index computes the scalar projection of a COBRA vector onto the TBI vector, quantifying how closely an individual's behavior matches typical TBI-related signs. Overall, the correlation between visual acuity and the TBI impairment index was not quite significant ($p=0.053$, $r=0.28$, Pearson's R), indicating that 92% of the variance in the TBI impairment index could not be attributed to static visual acuity problems.

To compute the overall detectability of TBI subjects using the two populations, computed the ROC curve area was computed for the two distributions (see FIG. 4A), which was 0.81. As control analyses, analogous ROC curve areas were computed for the subset of the TBI population (n=23) with visual acuity better than the 95$^{th}$ percentile of the control population (their detectability was still 0.80) and for the subset of the TBI population (n=29) that fell within the age range (20 to 56 years) of the control population (their detectability was still 0.83). This shows that the detection by COBRA that a given TBI subject is not within the normal population is not an indirect consequence of the negligible mismatches in acuity or age between the overall TBI and control populations.

The entire TBI population was also subdivided according to self-reported severity, and the ROC curve area was computed for each severity level separately (See FIG. 4B). For observers reporting "little to no residual injury" (severity level of 1), their TBI detectability (0.59) was not significantly different than chance (p >0.05, bootstrap test), although it cannot be ruled out that the TBI detectability value was actually slightly higher than 0.5. For observers reporting more severe symptoms (severity level ≥2), TBI detectability was observed ranging from 0.85 to 0.95 (average 0.91). Furthermore, across the entire TBI population, significant correlation was observed between self-reported severity and TBI impairment index (p<0.05, r=0.34, Pearson's R).

Observations Gleaned from Experiment

As shown above, a non-invasive, 15-minute Comprehensive Oculometric Behavioral Response Assessment (COBRA) task generates ten performance metrics that quantify an individual's dynamic visuomotor processing capability. Also as shown above, COBRA provides a sensitive screening tool for detecting and characterizing impairments associated with TBI, even years after recovery. First, COBRA was used to quantify the characteristic constellation of TBI-related deficits in a population of 34 TBI subjects, expressed as a vector (i.e., the TBI vector). Presumably, non-TBI brain pathologies will show different characteristic vectors. Second, the TBI vector was used to quantify each subject's functional neurological impairment. Third, these TBI impairment indices were used to evaluate how well COBRA can detect TBI-related signs.

For the entire TBI population, COBRA could discriminate TBI subjects from controls with 81% probability. For the nine TBI subjects who reported "little-to-no" residual injury, TBI impairment indices were not statistically distinguishable from those of control subjects (only 58% probability of detection). For the 25 TBI subjects who reported substantial residual effects, COBRA discriminated them with 91% probability.

In general, using oculomotor measures to screen for neural pathology may hold potential shortcomings since not all brain structures mediate visuomotor behavior. Whereas a punctate hippocampal tumor is unlikely to cause any discernable impairment on familiar oculomotor tasks, the diffuse nature of TBI suggests that visuomotor tasks, which require a wide swath of cortical and cerebellar circuitry to estimate, predict, and track precise motion trajectories, are well-suited to detect such injuries. Even mild, yet diffuse, insults to neural circuitry may degrade the quality of the final output behavior. However, the oculomotor deficits observed among TBI subjects may also reflect factors that co-occur with TBI (e.g., stroke, medications, depression).

That said, differing visual, cognitive, and motor demands (e.g., executive function, response inhibition, attention, perception, expectation, prediction, memory, etc.) of various oculomotor paradigms (e.g., predictive tracking, gap/overlap saccades, antisaccades, memory-guided saccades, gaze conjugacy, etc.) likely engage specific brain networks to differing degrees. In particular, different degrees of injury affecting different networks may be necessary for specific oculomotor signs to be observed in any particular task (e.g., saccadic hypometria, poor saccadic inhibition, gaze disconjugacy, altered saccade dynamics, etc.). For example, head injury cases presenting with ocular motor nerve palsy are more severe than those without, suggesting that certain oculomotor signs (e.g., gaze disconjugacy) may occur following a threshold level of damage to a localized set of brainstem structures (i.e., $III^{rd}$, $IV^{th}$, or $VI^{th}$ cranial nerves and their associated nuclei), resulting in greater difficulty in detecting milder cases. To assay neural processing across a diverse set of brain areas, the COBRA vector of some embodiments uses a wider array of behaviors to capture the entire neural hierarchy of visuomotor processing: initial pursuit latency and acceleration driven by retinal slip, later direction tuning determined by extrastriate cortical processing associated with perception, catch-up saccades driven by anticipated retinal position error, and steady-state motion processing driven by perceived object motion.

In the experimental data (see FIG. 2), the magnitude of the deficits observed in the ten COBRA metrics differed. Although all ten tested metrics had negative mean values, four did not significantly differ from control metrics and two were only mildly impacted, whereas the remaining four were severely impacted. Because they all had similar variance, these four metrics had more statistical power to detect TBI than the remaining six. The value of having a large set of largely-independent COBRA measures is to increase the likelihood of detecting different types of pathologies. To go one step further, as the relationship between structural damage and functional impairment becomes better understood by pairing behavioral tests like COBRA with structural scans, anatomical explanations for the relatively-high detection power of certain oculometrics for certain pathologies (e.g., speed responsiveness for TBI) may develop, as well as the reason that others (e.g., gaze disconjugacy) are only observed in more severe cases. Of course, more statistically powerful, as-yet undescribed, behavioral metrics may be discovered, and are intended to be incorporated within some embodiments as far as vectorizing multiple metrics. A value of the impairment index of some embodiments is that a single scalar distills the ten metrics along the single direction most consistent with TBI and can easily be refined and extended as additional valuable and independent dimensions are discovered.

It should be emphasized that COBRA metrics are not only able to detect TBI-related impairment (see FIG. 4A), they also reflect TBI severity as documented by self-report. As a population, normally-distributed TBI impairment indices were observed that overlap the control population (see FIG. 4A), largely due to those TBI subjects with "little-to-no" residual injury (see FIG. 4B), and leaving those TBI subjects with meaningful residual injuries (severity level >2) discriminable at 91%. However, future studies of acute TBI patients with more clinically-rigorous measures of the severity of their neurological impairment (e.g., the x-axis of a future FIG. 4B) may be beneficial to further demonstrate the value of COBRA in clinical triage settings.

Based on work showing tight linkages between visual perception/cognition and oculomotor responses, the familiar association in neurology between oculomotor behavior and the function of certain cranial nerves and their associated brainstem nuclei can be expanded to include the ten COBRA metrics as neurological indicators of dynamic visuomotor processing at several functional stages: from retinal transduction, to cortical circuitry supporting motion perception and spatial attention, to the cortico-brainstem-cerebellar pathways supporting sensorimotor action. It can be concluded that characteristic datasets aggregated from standardized oculomotor test batteries (such as COBRA) may allow clinicians to detect, quantify, and characterize impairments from transient brain insults (e.g., due to trauma, drug toxicity, or alcohol) as well as permanent injuries, to detect the onset of degenerative, developmental, and psychiatric disorders and track their progression, and to evaluate the effectiveness of candidate therapeutic interventions, even in the absence of an individual baseline.

FIG. 5 is a flowchart 500 illustrating a process for determining a type and severity of an individual's condition, according to an embodiment of the present invention. The process begins with creating search templates for various conditions at 510. These search templates may be derived by testing a baseline population with no known conditions and testing groups of individuals with a single known condition (e.g., glaucoma, certain brain cancers, different types of TBI, various degrees of sleep deprivation, various degrees of drug or alcohol intoxication, etc.). The search templates may be vectors with a direction and amplitude. More specifically, to form the search templates, raw measurements from multi-dimensional results obtained during testing (e.g., COBRA data) are vectorized and averaged across the population of individuals with a given condition to yield a TBI vector.

Once search templates have been derived, an individual of interest is subjected to oculometric testing at 520. The oculometric testing provides a multi-dimensional representation of the individual's performance on various visual tests. The multi-dimensional results of the individual's oculometric testing are then used to derive a COBRA vector for the individual at 530 that can then be compared to the "impairment vectors" of the search templates.

The dot product may provide a measure of alignment with the template vector. As such, it is a measure of the angular difference, as well as the amplitude of the individual's COBRA vector itself. A large amplitude and close alignment would yield large impairment indices. However, large amplitude with a wide misalignment yields small impairment index. This provides evidence that such a large impairment is not due to TBI.

Once the COBRA vector has been determined, it is compared to one or more search templates at 540. In other words, the COBRA vector for the individual is analyzed against one or more of the search templates to produce mappings of the vector to the one or more search templates. For instance, a computing system, may perform the comparison based on input from a neurologist or ophthalmologist, or the computing system may compare multiple (and perhaps many or all) search templates on its own to determine the most likely candidate or candidates for an individual's condition (or none at all if the individual does not correlate well with any condition's search template). The results of the analysis are then output for review at 550. For instance, by normalizing across the entire set of available search templates or by converting the impairment indices (in standard deviation units) into their corresponding p-score, the results may indicate that there is a 75% match with glaucoma, a 15% match with a concussion, a 5% match with diabetes, etc. A neurologist or ophthalmologist may then perform additional testing to confirm the condition, guided by the relative probabilities above.

Figure 6:
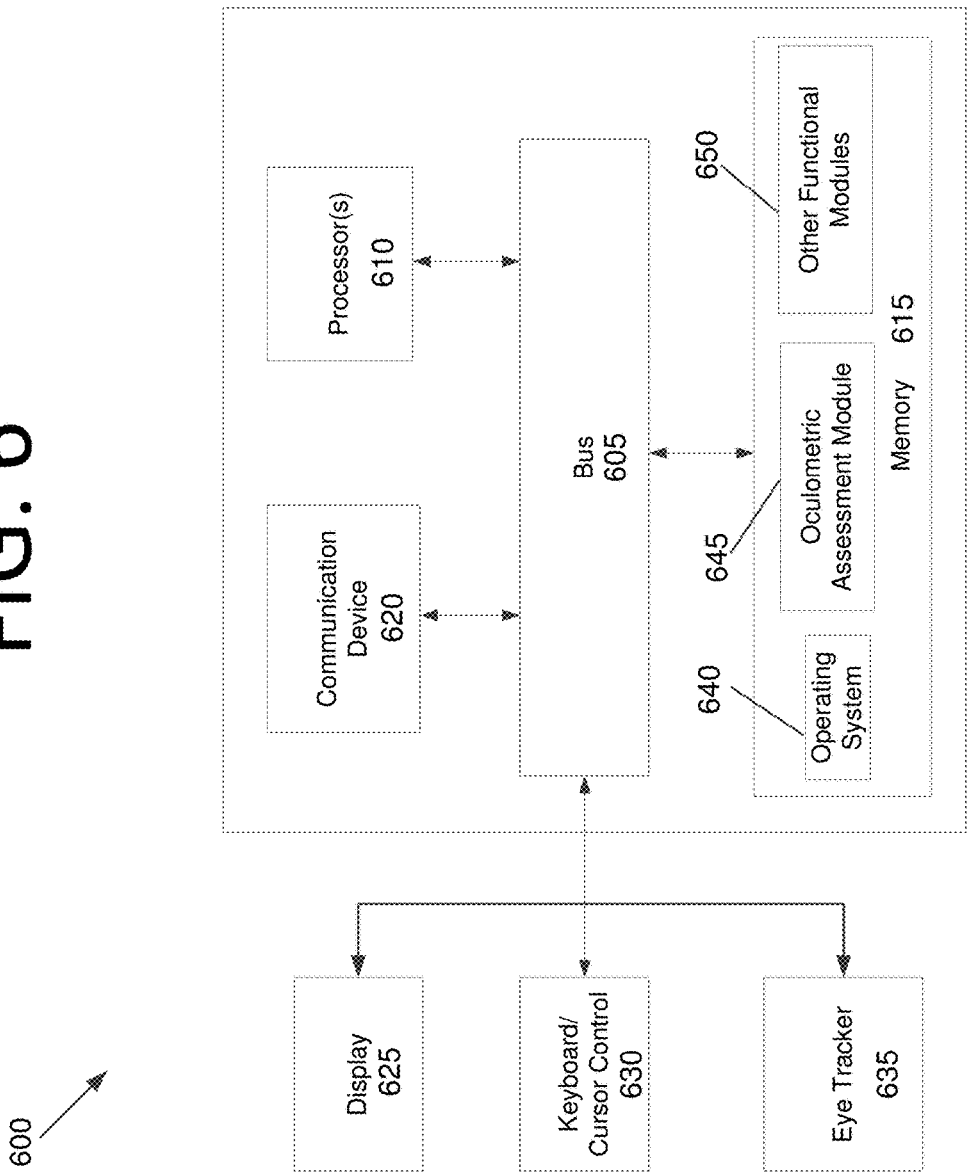
FIG. 6 is a block diagram of a computing system configured to perform oculometric assessment, according to an embodiment of the present invention.

FIG. 6 is a block diagram of a computing system 600 configured to perform oculometric assessment of sensorimotor impairment, according to an embodiment of the present invention. Computing system 600 includes a bus 605 or other communication mechanism for communicating information, and processor(s) 610 coupled to bus 605 for processing information. Processor(s) 610 may be any type of general or specific purpose processor, including a central processing unit (CPU) or application specific integrated circuit (ASIC). Processor(s) 610 may also have multiple processing cores, and at least some of the cores may be configured to perform specific functions. Multi-parallel processing may be used in some embodiments. Computing system 600 further includes a memory 615 for storing information and instructions to be executed by processor(s) 610. Memory 615 can be comprised of any combination of random access memory (RAM), read only memory (ROM), flash memory, cache, static storage such as a magnetic or optical disk, or any other types of non-transitory computer-readable media or combinations thereof. Additionally, computing system 600 includes a communication device 620, such as a transceiver and antenna, to wirelessly provide access to a communications network.

Non-transitory computer-readable media may be any available media that can be accessed by processor(s) 610 and may include both volatile and non-volatile media, removable and non-removable media, and communication media. Communication media may include computer-readable instructions, data structures, program modules or other data in a modulated data signal such as a carrier wave or other transport mechanism and includes any information delivery media.

Processor(s) 610 are further coupled via bus 605 to a display 625, such as a Liquid Crystal Display (LCD), for displaying information to a user. A keyboard and cursor control device 630, such as a computer mouse, are further coupled to bus 605 to enable a user to interface with computing system. However, in certain embodiments such as those for mobile computing implementations, a physical keyboard and mouse may not be present, and the user may interact with the device solely through display 625 (or virtual reality system) and/or a touchpad (not shown). Any type and combination of input devices may be used as a matter of design choice. An eye tracker 635 provides measurements of user eye position for the purposes of oculometric testing.

Memory 615 stores software modules that provide functionality when executed by processor(s) 610. The modules include an operating system 640 for computing system 600. The modules further include an oculometric assessment module 645 that is configured to analyze measurements of user eye movements, determine a disease vector for the user, and compare the disease vector to one or more search templates to determine a degree of matching to one or more conditions. Computing system 600 may include one or more additional functional modules 650 that include additional functionality.

One skilled in the art will appreciate that a "system" could be embodied as an embedded computing system, a personal computer, a server, a console, a personal digital assistant (PDA), a cell phone, a tablet computing device, a virtual or augmented reality headset, or any other suitable computing device, or combination of devices. Presenting the above-described functions as being performed by a "system" is not intended to limit the scope of the present invention in any way, but is intended to provide one example of many embodiments of the present invention. Indeed, methods, systems and apparatuses disclosed herein may be implemented in localized and distributed forms consistent with computing technology, including cloud computing systems.

It should be noted that some of the system features described in this specification have been presented as modules, in order to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, RAM, tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

The process steps performed in FIG. 5 may be performed by a computer program, encoding instructions for the non-linear adaptive processor to perform at least the process described in FIG. 5, in accordance with embodiments of the present invention. The computer program may be embodied on a non-transitory computer-readable medium. The computer-readable medium may be, but is not limited to, a hard disk drive, a flash device, RAM, a tape, or any other such medium used to store data. The computer program may include encoded instructions for controlling the nonlinear adaptive processor to implement the process described in FIG. 5, which may also be stored on the computer-readable medium.

The computer program can be implemented in hardware, software, or a hybrid implementation. The computer program can be composed of modules that are in operative communication with one another, and which are designed to pass information or instructions to display. The computer program can be configured to operate on a general purpose computer, or an ASIC.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A computer-implemented method for improved detection of clinical conditions for individuals, comprising:

creating search templates for a plurality of clinical conditions, by a computing system, each search template comprising a vector in multi-dimensional space indicative of a respective clinical condition;

receiving, by the computing system, oculometric testing data collected from oculometric testing, the oculometric testing data including data collected from a randomized, radial tracking task performed on an individual and a plurality of oculometric measures collected from the individual;

creating a vector for the individual, by the computing system, based on the oculometric testing data;

analyzing the vector for the individual, by the computing system, against one or more of the search templates; and producing an impairment index that is a projection of the vector for the individual onto the one or more search templates based on the analyzing,
wherein
the step of producing the impairment index comprises taking a dot product of the vector for the individual and each search template and dividing the dot product by a scaling factor, and
wherein the impairment index is a scalar measure of severity of the individual's clinical condition.

2. The computer-implemented method of claim 1, wherein the search templates are derived by testing a baseline population with no specific known abnormal conditions and testing groups of individuals with a single specific known abnormal condition for each respective search template.

3. The computer-implemented method of claim 2, wherein the creating of the search templates comprises vectorizing and averaging raw measurements from data obtained during testing across a population of individuals to yield the search template vector with a direction and an amplitude.

4. The computer-implemented method of claim 1, wherein the oculometric testing yields a multi-dimensional representation of the individual's performance on a plurality of visual tests.

5. The computer-implemented method of claim 1, wherein the vector for the individual comprises a multi-dimensional Comprehensive Oculometric Behavioral Response Assessment (COBRA) vector having a direction and an amplitude.

6. The computer-implemented method of claim 1, further comprising:
displaying ranked results, by the computing system, in an order from a most likely match to a least likely match.

7. The computer-implemented method of claim 1, wherein the creating of each search template further comprises:
determining, by the computing system, a raw Comprehensive Oculometric Behavioral Response Assessment (COBRA) vector comprising a plurality of measurements for each individual having a condition associated with the search template;
converting the plurality of measurements, by the computing system, into z-values relative to control data from a baseline population using:

$$\omega = \frac{RAW - CONTROL_{50th}}{\sigma}$$

where $\omega$ is a standard normalized metric, $$\sigma = \frac{(CONTROL_{75th} - CONTROL_{25th})}{2 \cdot \Phi^{-1}(0.75)},$$

and $\Phi^{-1}$ is the inverse of a normal cumulative distribution function.

8. The computer-implemented method of claim 1, wherein each search template is determined by:

$$\sum_{i=1}^{n} \frac{(COBRA_i)}{n}$$

where $COBRA_i$ is a Comprehensive Oculometric Behavioral Response Assessment (COBRA) vector for each individual with a given condition for the search template and n is a number of subject with the condition.

9. The computer-implemented method of claim 1, wherein the scaling factor is given by:

SCALING FACTOR=‖CHOL(COV(CONTROL)) ·TBI'‖ where CHOL is the Cholesky Decomposition, COV (CONTROL) is the covariance matrix of the population of control COBRA vectors, and TBI' is the transpose of the TBI vector.

10. A non-transitory computer-readable medium storing a computer program, the program configured to cause at least one processor to:
receive oculometric testing data collected from oculometric testing, the oculometric testing data including data collected from a randomized, radial tracking task performed on an individual and a plurality of oculometric measures collected from the individual;
create a vector for the individual based on the oculometric testing data;
analyze the vector for the individual against a search template;
produce an impairment index that is a projection of the vector for the individual onto the search template based on the analyzing, the search template comprising a vector in multi-dimensional space indicative of a respective condition,
wherein to produce the impairment index comprises determining the impairment index by taking a dot product of the vector for the individual and each search template and dividing the dot product by a scaling factor, and wherein the impairment index is a scalar measure of severity of the individual's clinical condition.

11. The non-transitory computer-readable medium of claim 10, wherein the oculometric testing yields a multi-dimensional representation of the individual's performance on a plurality of visual tests.

12. The non-transitory computer-readable medium of claim 10, wherein the vector for the individual comprises a multi-dimensional Comprehensive Oculometric Behavioral Response Assessment (COBRA) vector having a direction and an amplitude.

13. The non-transitory computer-readable medium of claim 10, wherein the program is further configured to cause the at least one processor to:
create the search template by vectorizing and averaging raw measurements from data obtained during testing across a population of individuals to yield the search template vector with a direction and an amplitude, wherein the search template is derived by testing a baseline population with no specific known abnormal conditions and testing a group of individuals with a single specific known abnormal condition associated with the search template.

14. The non-transitory computer-readable medium of claim 10, wherein the scaling factor is given by:

SCALING FACTOR=‖CHOL(COV(CONTROL)) ·TBI'‖ where CHOL is the Cholesky Decomposition, COV (CONTROL) is the covariance matrix of the population of control COBRA vectors, and TBI' is the transpose of the TBI vector.

15. A computing system, comprising:
memory storing computer program code for performing oculometric assessment of sensorimotor impairment; and
at least one processor configured to execute the computer program code, the computing system configured to:
receive oculometric testing data collected from oculometric testing, the oculometric testing data including data collected from a randomized, radial tracking task performed on an individual and a plurality of oculometric measures collected from the individual;
create a vector for the individual based on the oculometric testing data;
analyze the vector for the individual against a search template, the search template comprising a vector in multi-dimensional space indicative of a respective condition, and
produce an impairment index based on the analysis that is a projection of the vector for the individual onto the search template based on the analyzing, wherein to produce the impairment index comprises determining the impairment index by taking a dot product of the vector for the individual and each search template and dividing the dot product by a scaling factor, and wherein the impairment index is a scalar measure of severity of the individual's clinical condition.

16. The computing system of claim 15, wherein the vector for the individual comprises a multi-dimensional Comprehensive Oculometric Behavioral Response Assessment (COBRA) vector having a direction and an amplitude.

17. The computing system of claim 15, wherein the computing system is further configured to:
create the search template by vectorizing and averaging raw measurements from data obtained during testing across a population of individuals to yield the search template vector with a direction and an amplitude, wherein the search template is derived by testing a baseline population with no specific known abnormal conditions and testing a group of individuals with a single specific known abnormal condition associated with the search template.

18. The computing system of claim 15, wherein the scaling factor is given by:

$$\text{SCALING FACTOR} = \|\text{CHOL}(\text{COV}(\text{CONTROL})) \cdot \text{TBI}'\|$$

where CHOL is the Cholesky Decomposition, COV (CONTROL) is the covariance matrix of the population of control COBRA vectors, and TBI' is the transpose of the TBI vector.

* * * * *